(12) United States Patent
Heljenek

(10) Patent No.: US 6,464,726 B1
(45) Date of Patent: Oct. 15, 2002

(54) BREAST IMPLANT SYSTEM AND METHOD OF AUGMENTATION

(76) Inventor: Jenna Heljenek, 79 Eayrestown Rd, Medford, NJ (US) 08055

( * ) Notice: Subject to any disclaimer, the term of this patent is extended or adjusted under 35 U.S.C. 154(b) by 0 days.

(21) Appl. No.: 09/615,820

(22) Filed: Jul. 13, 2000

(51) Int. Cl.$^7$ .................................................. A61F 2/12
(52) U.S. Cl. ............................................................ 623/8
(58) Field of Search ........................................ 623/7, 8

(56) References Cited

U.S. PATENT DOCUMENTS

| | | | |
|---|---|---|---|
| 4,433,440 A | * | 2/1984 | Cohen ............................ 623/8 |
| 4,643,733 A | * | 2/1987 | Becker ........................... 623/8 |
| 5,026,394 A | * | 6/1991 | Baker ............................. 623/8 |
| 5,147,398 A | * | 9/1992 | Lynn et al. ..................... 623/8 |
| 5,236,454 A | * | 8/1993 | Miller ............................ 623/8 |
| 5,246,454 A | * | 9/1993 | Peterson ........................ 623/8 |
| 5,630,842 A | * | 5/1997 | Brodniewicz .................. 623/8 |
| 5,855,588 A | * | 1/1999 | Young ......................... 606/190 |
| 6,055,989 A | * | 5/2000 | Rehnke ........................ 128/898 |
| 6,228,116 B1 | * | 5/2001 | Ledergerber ................... 623/8 |

* cited by examiner

Primary Examiner—David J. Isabella
Assistant Examiner—Will H Matthews
(74) Attorney, Agent, or Firm—LaMorte & Associates, P.C.

(57) ABSTRACT

A system and method for augmenting a woman's breasts is claimed. The system includes two separate breast prostheses that are used to enhance each single breast. A first breast prosthesis is surgically implanted under the pectoral muscle behind the breast. The first breast prothesis augments the posterior section of the breast nearest the chest. A second breast prosthesis is provided that is surgically implanted between the breast tissue and the pectoral muscle. The second breast prosthesis augments the anterior section of the breast in front of the pectoral muscle. The second breast prosthesis provides the breast with a large size and soft texture, while the first breast prosthesis helps blend the augmented breast into the chest for a more natural appearance.

14 Claims, 2 Drawing Sheets

BREAST IMPLANT SYSTEM AND METHOD OF AUGMENTATION

BACKGROUND OF THE INVENTION

1. Field of the Invention

The present invention relates to prosthetic breast implants that are used for breast augmentation and breast reconstruction. More particularly, the present invention relates to the structure of the breast implants and the surgical techniques used during augmentation or reconstructive surgery.

2. Description of the Prior Art

Breast augmentation surgeries and breast reconstructive surgeries have become commonplace within the last twenty years. In a breast augmentation procedure, a breast prosthesis is implanted into the chest to enhance the apparent size of the naturally occurring breast tissue. In a breast reconstructive procedure, a breast prosthetic is used to replace the diseased breast tissue after the diseased breast tissue has been surgically removed.

Breast augmentation procedures and breast reconstructive procedures usually are performed using one of three common surgical techniques. The simplest of the surgical techniques is that used in the "over the muscle" breast augmentation procedure. Using such a technique, a single breast prosthesis is placed between the pectoral muscle in the chest and the mammary glands. In such a procedure, the breast prosthesis is in complete contact with the breast tissue, but is unsupported by any muscle.

The advantages of this procedure include ease of surgery, avoidance of mastopexy in mild ptosis and less post-operative discomfort. This type of operation also enables oversized implants to be used in order to obtain unnaturally large breasts if desired.

The disadvantages of the "over the muscle" procedure include the fact that the augmented breasts have a rounded appearance that appear somewhat unnatural. Furthermore, since the breast prosthesis is only supported by breast tissue, the breasts tend to sag over time.

The second technique used in breast augmentation surgery is a partial submuscular implant procedure. In this procedure, a breast prosthesis is placed partially under the pectoral muscle through either an incision in the nipple or an inframammary crease incision. During surgery, the muscle support fascia at the bottom of the pectoral muscle is disrupted and the breast prosthesis is partially inserted under the muscle. The result is that the top of the breast prosthesis is covered by the pectoral muscle and the bottom is not. This allows the bottom of the augmented breast to appear round while the top of the chest appears more natural.

Some of the disadvantages of the partial submuscular procedure are that it requires a more complex surgical procedure than does an "over the muscle" surgery. Furthermore, since the breast prosthesis is partially under the muscle, there are size limitations on the breast prosthesis. Lastly, since the bottom of the breast prosthesis is unsupported by the pectoral muscle, the augmented breast may have a tendency to sag over time.

The third technique used in breast surgery is the completely under the muscle technique. In this technique, the intra-muscle support fascia of the pectoral muscle is not cut. Rather, the breast prosthesis is placed entirely under the pectoral muscle and is supported by the muscle facia at the bottom.

The "under the muscle technique" provides a natural looking breast. However, the implants are limited in size. Furthermore, the breasts tend to be painful until the muscle support fascia stretches.

In all of the surgical techniques mentioned above, a single breast prosthesis is placed in each breast. Because of the use of a single breast prosthesis in an "over the muscle" procedure, unnaturally round breasts occur. Because of the use of a single breast prosthesis per breast in the partial and complete "under the muscle" procedures, size limitations in the prosthesis are an issue.

A need therefore exists in the art for a breast prosthesis system that uses more than one prosthesis per breast, thereby combining the advantages of the over the muscle and under the muscle augmentation techniques while minimizing the disadvantages of each. This need is met by the present invention as described and claimed below.

SUMMARY OF THE INVENTION

The present invention is a system and method for breast augmentation. The system includes two separate breast prostheses that are used to enhance a single breast. A first breast prosthesis is surgically implanted under the pectoral muscle behind the breast. The first breast prothesis augments the posterior section of the breast nearest the chest. A second breast prosthesis is provided that is surgically implanted between the pectoral muscle and the breast tissue. The second breast prosthesis augments the anterior section of the breast in front of the pectoral muscle. The second breast prosthesis provides the breast with a large size and soft texture, while the first breast prosthesis helps blend the augmented breast into the chest for a more natural appearance.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE INVENTION

Figure 1:
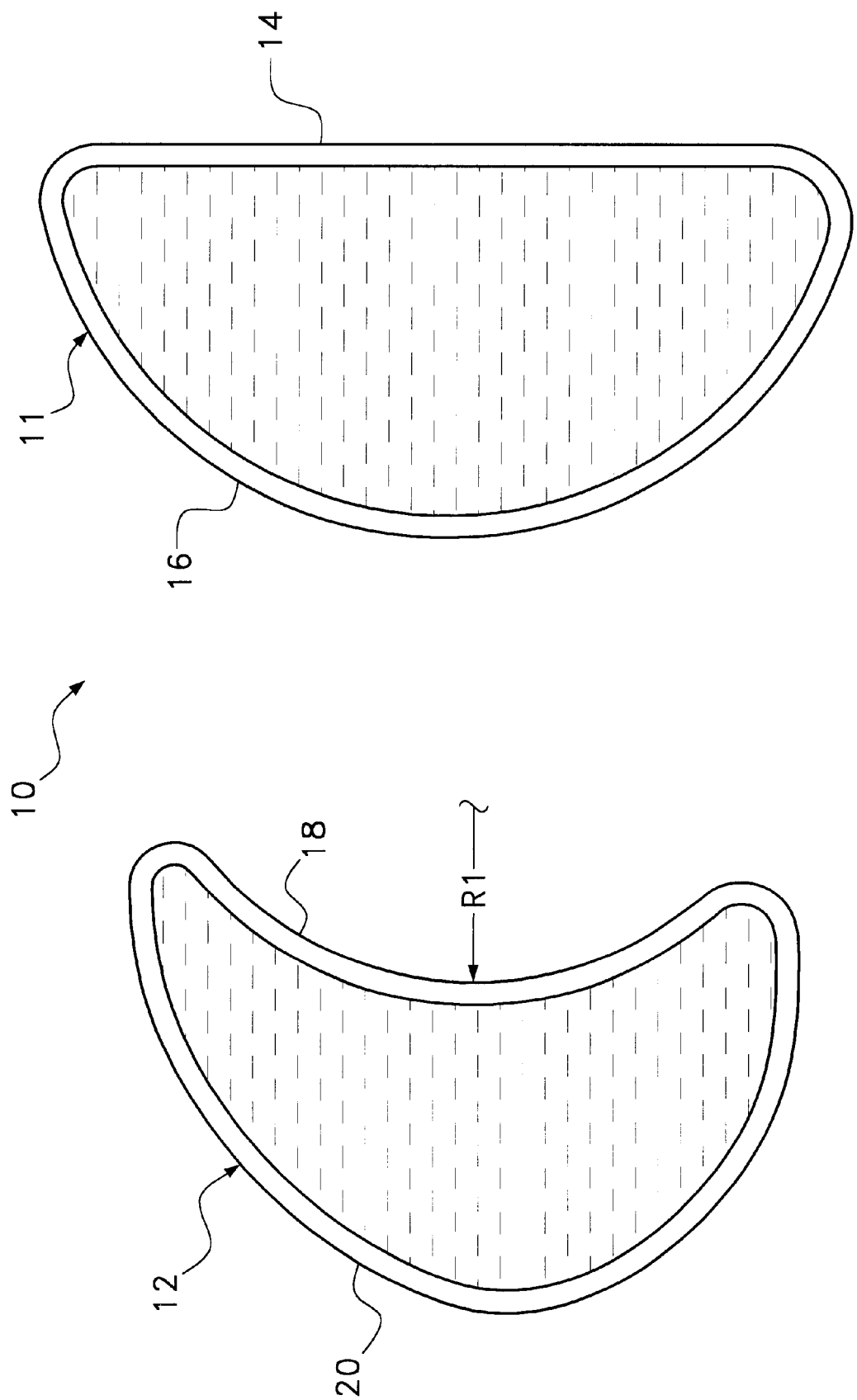
FIG. 1 is a cross-sectional view of two matched breast prostheses used in the present invention augmentation system, wherein both breast prostheses are used in a single breast.

Referring to FIG. 1, there is shown a cross-section of two breast prostheses 11, 12 used as part of the present invention system 10. The two breast prostheses 11, 12 are used to augment a single breast. The first breast prosthesis 11 is molded to have a generally plane surface 14 and a generally convex surface 16. The first breast prosthesis 11 can be made of any known material currently approved for use in breast implants by the Food & Drug Administration (FDA). The first breast prosthesis can be solid but is preferably filled with a liquid, such as saline, as is shown in FIG. 1. If the first breast prosthesis were solid, it would be molded of an elastomeric material approved for such applications by the FDA.

The second breast prosthesis 12 has a generally concave surface 18 and an opposite convex surface. The radius of curvature R1 of the concave surface 18 is greater than or equal to the external radius of curvature of the convex surface 16 of the first breast prosthesis 11. The second breast prosthesis 12 is also made from FDA approved materials and is preferably filled with a liquid, such as saline.

Figure 2:
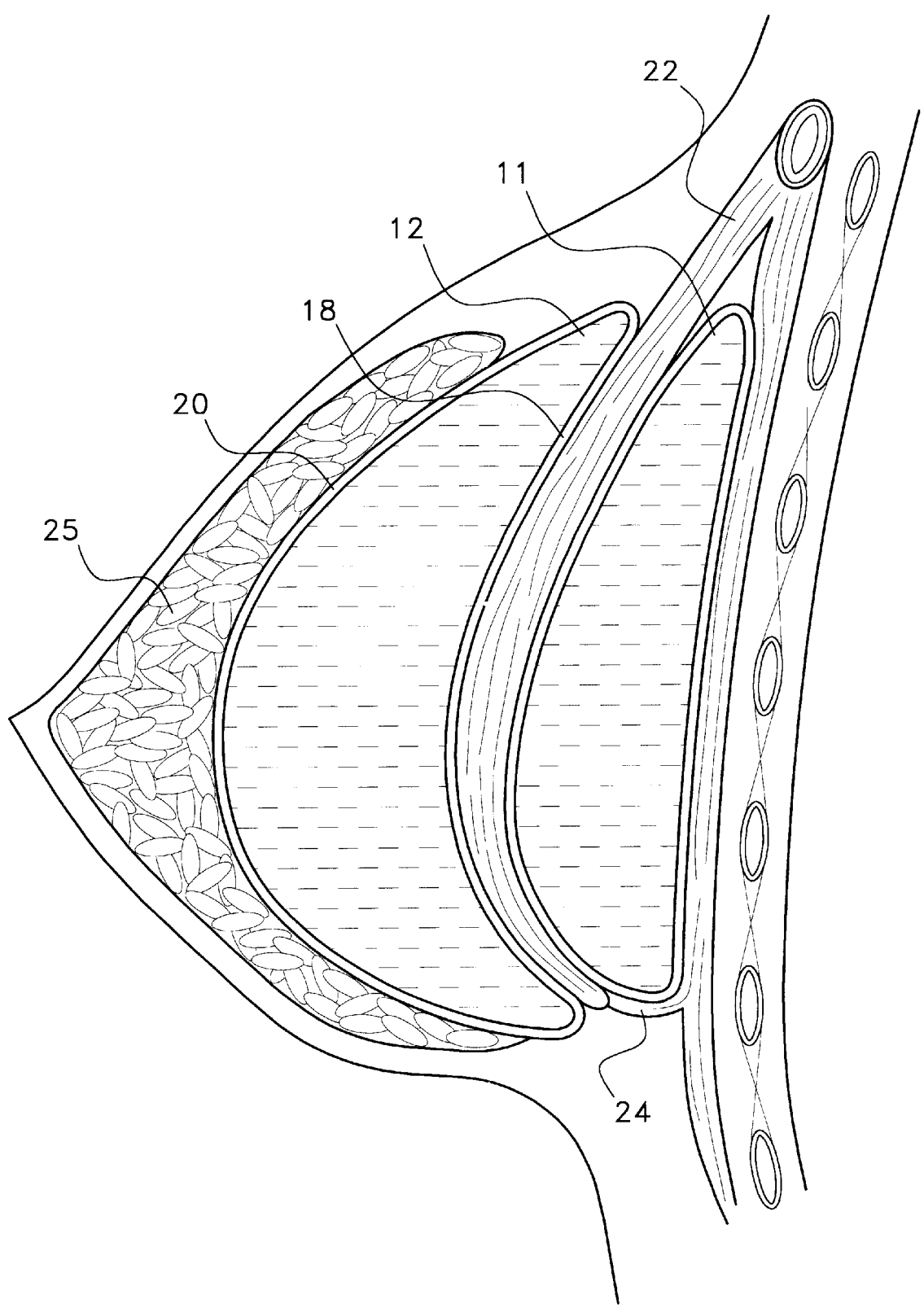
FIG. 2 is a cross-sectional view of a person's chest, having a breast augmented using the present invention system and method.

Referring to FIG. 2, it can be seen that the first breast prosthesis 11 is surgically placed completely under the pectoral muscle 22 behind the breast. The first breast prosthesis 11 is inserted under the pectoral muscle 22 using traditional surgical techniques, wherein an incision is made in the pictorial muscle 22 in the anterior axillary fold. Once the first breast prosthesis 11 is inserted under the pectoral muscle 22, the first breast prosthesis 11 is completely covered by the pectoral muscle 22. The bottom of the first breast prosthesis 11 is supported by the muscle support fascia 24.

The presence of the first breast prosthesis 11 under the pectoral muscle 22, extends the pectoral muscle 22 away from the body. As such, the exterior of the pectoral muscle 22 is more convex in shape. The second breast prosthesis 12 is surgically placed over the pectoral muscle 22 in the sub-glandular position. The second breast prosthesis 22 can be inserted through the same incision as the first breast prosthesis 11 or can be inserted through a secondary incision.

The concave surface 18 of the second breast prosthesis 12 conforms around the artificially extended convex surface of the pectoral muscle 22. The convex surface 20 of the second breast prosthesis 12 augments the breast tissue 25 at the front end of the breast.

Since the second breast prosthesis 12 is not positioned behind the pectoral muscle 22, there are no size limitations to the second breast prosthesis 12. The second breast prosthesis 12 can therefore be as large as is desired by the woman having the augmentation surgery. The purpose of the first breast prosthesis 11 is to enhance the size and shape of the pectoral muscle 22 supporting the second breast prosthesis 12. As a result, the first breast prosthesis 11 helps blend the chest into the augmented breast. The result is that the breast tends to look more natural and less ball-like, even though the combined size of the. first and second breast prostheses 11, 12 may be significant.

The advantages of the present invention breast implant system include the fact that the breast can be augmented to large sizes, while still having a natural appearance. Furthermore, it is the combined size of the first and second breast prostheses 11, 12 that give the breast its new size. The size of the first breast prosthesis 11 therefore represents only a portion of the total augmentation. The size of the first breast prosthesis 11 can therefore be minimized to only what is needed to make the second breast prosthesis appear natural. Since the size of the first breast prosthesis 11 is minimized, the stretching of the pectoral muscle 22 support fascia 24 is minimized. This results in a quicker recovery from the surgery.

The first breast prosthesis 11 and the second breast prosthesis 12 will come in matched sets. Depending upon the diameter of the breast, the stature of the woman, the initial size of the breast and the desired size of the breast, a surgeon can select the set of breast prostheses that are correct for the patient.

Once the sets of breast prostheses are selected, the surgical procedure is as follows. First, an incision is made and the first breast prosthesis 11 is inserted under the pectoral muscle 22 where it lies closest to the skin at the anterior axillary fold. Although the initial incision can then be used introduce the second breast prosthesis 12, the initial incision is preferably closed and a second incision made. The second incision can be made under the breast, at the nipple or even at the naval. The second breast prosthesis 12 is then inserted through the second incision into the breast. The second breast prosthesis 12 is interposed between the exterior of the pectoral muscle 22 and the existing breast tissue. The second breast prosthesis 12 is then properly oriented and the second incision closed.

Since the present invention procedure contains two distinct steps, the procedure can be performed at two different times. A patient may have the first breast prosthesis implanted under the pectoral muscle in both breasts. After a predetermined time to heal, the patient can return for the implanting of the second breast prosthesis over the pectoral muscle. In this manner, the breast augmentation can be made to appear gradual, thereby providing the patient with a time frame in which to adjust to the anatomical change.

It will be understood that the specifics of the breast prosthesis and surgical procedure described above illustrates only one exemplary embodiment of the present invention. A person skilled in the art can therefore make numerous alterations and modifications to the shown embodiment and procedure utilizing functionally equivalent techniques. All such modifications are intended to be included within the scope of the present invention as defined by the appended claims.

What is claimed is:

1. A method of breast augmentation, comprising the steps of:
   providing a first breast prosthesis;
   surgically implanting said first breast prosthesis completely under the pectoral muscle behind a breast, without disruption to the muscle support fascia at the bottom of the pectoral muscle;
   providing a separate second breast prosthesis;
   surgically implanting said second breast prosthesis between the pectoral muscle and the breast, wherein said first breast prosthesis and said second breast prosthesis combine to increase the apparent size of the breast on the body.

2. The method according to claim 1, wherein said step of surgically implanting said first breast prosthesis includes making a first incision and inserting said first prosthesis under the pectoral muscle through said first incision.

3. The method according to claim 2, wherein said step of surgically implanting said second breast prosthesis includes making a second incision and inserting said second breast prosthesis through said second incision to a position between the breast and the pectoral muscle.

4. The method according to claim 1, wherein said second breast prosthesis has a concave surface that abuts against the pectoral muscle and a convex surface that faces the breast.

5. The method according to claim 1, wherein said first breast prosthesis and said second breast prosthesis concentrically align when surgically implanted.

6. The method according to claim 1, wherein said first breast prosthesis is and said second breast prosthesis are both liquid filled.

7. The method according to claim 1, wherein said first breast prosthesis is made of elastomeric material and said second breast prosthesis is liquid filled.

8. A method of augmenting a breast, including the steps of:
   placing a first breast prosthesis under the pectoral muscle behind a breast, without disrupting the muscle support fascia at the bottom of the pectoral muscle;
   placing a separate second breast prosthesis between the breast and the pectoral muscle in the same breast, wherein said first breast prosthesis and said second breast prosthesis combine to augment the size of the breast.

9. The method according to claim 8, wherein said first breast prosthesis and said second breast prosthesis concentrically align when implanted.

10. The method according to claim 8, wherein said first breast prosthesis and said second breast prosthesis are both liquid filled.

11. The method according to claim 8, wherein said first breast prosthesis is made of elastomeric material and said second breast prosthesis is liquid filled.

12. The method according to claim 8, wherein said step of placing said first breast prosthesis includes making a first incision and inserting said first prosthesis under the pectoral muscle through said first incision.

13. The method according to claim 12, wherein said step of placing said second breast prosthesis includes making a second incision and inserting said second breast prosthesis through said second incision to a position between the breast and the pectoral muscle.

14. The method according to claim 8, wherein said second breast prosthesis has concave surface that abuts against the pectoral muscle and a convex surface that faces the breast.

* * * * *